United States Patent [19]

Stumpp et al.

[11] Patent Number: 4,983,773
[45] Date of Patent: Jan. 8, 1991

[54] PREPARATION OF BIS-(4-CHLOROPHENYL) SULFONE

[75] Inventors: Michael Stumpp, Deidesheim; Peter Neumann, Mannheim; Heinz Eilingsfeld, Frankenthal, all of Fed. Rep. of Germany

[73] Assignee: BASF Aktiengesellschaft, Ludwigshafen, Fed. Rep. of Germany

[21] Appl. No.: 417,448

[22] Filed: Oct. 5, 1989

[30] Foreign Application Priority Data

Oct. 19, 1988 [DE] Fed. Rep. of Germany ....... 3835562

[51] Int. Cl.$^5$ ............................................. C07C 147/06
[52] U.S. Cl. ....................................... 568/034; 562/83
[58] Field of Search ........................ 568/34, 33; 562/83

[56] References Cited

U.S. PATENT DOCUMENTS

| 3,052,708 | 9/1962 | Velluz et al. | 568/34 |
|---|---|---|---|
| 3,415,887 | 12/1968 | Keogh, et al. | 568/34 |
| 3,579,590 | 5/1971 | Davis | 568/34 |
| 3,673,259 | 6/1972 | Rosin et al. | 568/34 |
| 3,855,312 | 12/1974 | Horner | 568/34 |
| 3,870,685 | 3/1975 | Jones et al. | 528/336 |
| 4,172,852 | 10/1979 | Ark et al. | 568/34 |
| 4,778,932 | 10/1988 | Manami et al. | 568/33 |
| 4,822,916 | 4/1989 | Aaronson et al. | 568/34 |

FOREIGN PATENT DOCUMENTS

| 1221376 | 12/1984 | Canada . | |
| 0147298 | 7/1985 | European Pat. Off. . | |
| 1950394 | 4/1970 | Fed. Rep. of Germany . | |
| 2252571 | 5/1974 | Fed. Rep. of Germany . | |
| 3723401 | 1/1988 | Fed. Rep. of Germany . | |
| 1572916 | 8/1980 | United Kingdom | 568/34 |

OTHER PUBLICATIONS

The Journal of the American Chemical Society, vol. 76, 1954, pp. 5491–5494, P. Kovacic, et al., "Chlorination of Aromatic Compounds with Metal Chlorides".

The Journal of Organic Chemistry, vol. 32, 1967, pp. 2931–2933, B. M. Graybill, "The Synthesis of Aryl Sulfones".

*Primary Examiner*—Mary E. Ceperley
*Attorney, Agent, or Firm*—Oblon, Spivak, McClelland, Maier & Neustadt

[57] ABSTRACT

Bis-(4-chlorophenyl) sulfone is prepared by reacting chlorobenzene with sulfuric acid at from 200° to 250° C. by a process in which a condensing agent is added.

3 Claims, No Drawings

PREPARATION OF BIS-(4-CHLOROPHENYL) SULFONE

The present invention relates to a novel process for the preparation of bis-(4-chlorophenyl) sulfone by reacting chlorobenzene with sulfuric acid in the presence of a condensing agent.

Bis-(4-chlorophenyl) sulfone is an important intermediate which is used mainly for the preparation of aromatic polysulfones and for the synthesis of bis-(aminophenyl) sulfone, which is required both for the therapy of leprosy and for curing epoxy resins. For this intended use, it is essential that the bis-(4-chlorophenyl) sulfone is of high purity.

Bis-(4-chlorophenyl) sulfone can be prepared, for example by the process described in DE-A No. 1 087 592, by reacting chlorobenzene with a mixture of sulfur trioxide and dimethyl or diethyl pyrosulfate (cf. U.S. Pat. No. 3, 415, 887). However, this process uses dimethyl sulfate, which, owing to its toxicity, is unacceptable.

The most well known method for the preparation of bis-(4-chlorophenyl) sulfone is the Friedel-Crafts reaction of 4-chlorobenzenesulfonyl chloride with chlorobenzene, the catalyst used being, for example, iron(III) chloride. In this procedure, which is described in, for example, DE-A No. 2 704 972 or U.S. Pat. No. 4, 172, 852, the use of iron(III) chloride is disadvantageous. The reaction to give the sulfone is carried out in chlorobenzene as a solvent at about 140° C. However, J. Am. Chem. Soc. 76 (1984), 5491 discloses that iron(III) chloride also acts as a chlorinating agent for chlorobenzene at this temperature, so that considerable amounts of dichlorobenzenes are formed as byproducts, necessitating expensive working up, since dichlorobenzenes too can react with chlorobenzenesulfonyl chloride to give undesirable sulfones.

If the reaction is carried out as a single-stage reaction starting from chlorobenzene, without isolation of the intermediate chlorobenzenesulfonyl chloride, care must be taken to ensure that sulfonic acid, thionyl chloride and sulfur chlorides (as an impurity in the thionyl chloride) are no longer present in the reaction mixture, since the free sulfonic acid causes deactivation of the catalyst and thionyl chloride and sulfur chlorides likewise lead to undesirable byproducts. A further difficulty is that N,N-dimethylformamide is required for complete conversion of chlorobenzenesulfonic acid with thionyl chloride into the corresponding sulfonyl chloride, carcinogenic N,N-dimethylcarbamyl chloride being formed as a byproduct. In addition, the iron chloride must then be removed from the reaction mixture by hydrolysis. On the one hand, a very corrosive medium, which sets high requirements for the materials used, is obtained, and on the other hand fairly large amounts of chlorobenzene enter the aqueous phase in this procedure, with the result that the wastewater has to be worked up.

DE-A No. 2 252 571 describes the synthesis of bis-(4-chlorophenyl) sulfone from chlorobenzene and chlorobenzenesulfonic acid. At from 220° to 260° C. at superatmospheric pressure, bis-(4-chlorophenyl) sulfone is obtained in good yield but in relatively long reaction times.

It is an object of the invention to provide a process for the preparation of bis-(4-chlorophenyl) sulfone from chlorobenzene and sulfuric acid, which process is improved with regard to selectivity and space-time yield.

We have found that this object is achieved if a condensing agent is added during the preparation of bis-(4-chlorophenyl) sulfone by heating a mixture of chlorobenzene and sulfuric acid to 200°–250° C.

Examples of suitable condensing agents are boric acid and trifluoromethanesulfonic acid.

The formation of bis-(4-chlorophenyl) sulfone from chlorobenzene and sulfuric acid takes place in two condensation steps:

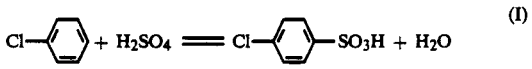

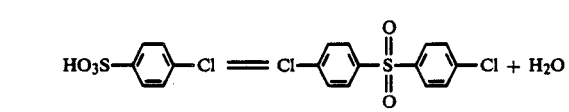

As generally known and described in, for example, DE-A No. 2 252 571, the first condensation step, i.e. the sulfonation reaction (I), takes place very much more rapidly than the sulfone formation (II). However, because of the low reactivity of chlorobenzene, both condensation steps require severe reaction conditions. As described in J. Org. Chem. 32 (1967), 2931, no reaction of chlorobenzene with p-toluenesulfonic acid is observed at 80° C., even with the addition of polyphosphoric acid.

The effect of the reaction temperature on the formation of bis-(4-chlorophenyl) sulfone is also described in DE-A No. 2 252 571. However, the reaction takes place so slowly at 220°–260° C. that a long reaction time is necessary for a reasonable conversion.

According to the invention, the reaction time can be considerably reduced if a condensing agent is added to the reaction mixture, in particular in a catalytic amount.

Since the condensation steps (I) and (II) are reversible, it is advantageous to remove the water formed in the reaction from the reaction mixture by azeotropic distillation. The entraining agent is thereafter generally recycled continuously to the reaction mixture. The entraining agent used is, as a rule, chlorobenzene.

The reaction conditions are advantageously chosen so that a pressure of from 4 to 5 bar is maintained. To maintain the boiling conditions, the temperature is increased continuously from 200° to 250° C. during the azeotropic distillation. However, the boiling conditions can also be achieved isothermally by reducing the pressure at a constant temperature.

As a result of the addition of catalytic amounts of boric acid, for example, the reaction time is reduced by 10 hours for 68% conversion (6 hours compared with 16 hours in the absence of a condensing agent); after a reaction time of 10 hours, a conversion of 84% is obtained.

The addition of trifluoromethanesulfonic acid gives similar results.

Surprisingly, we have furthermore found that the addition of a condensing agent also has an advantageous effect on the isomer distribution of the diphenyl sulfones formed. The following isomer distributions were found:

|  | 4,4'- | 2,4'- | 3,4'-isomer |
|---|---|---|---|
| Without the addition of a condensing agent | 79% | 7.5% | 13.5% |
| With the addition of boric acid | 84.8% | 7.8% | 7.4% |
| With the addition of trifluoromethanesulfonic acid | 89.3% | 5.2% | 5.5% |

By adding boric acid or trifluoromethanesulfonic acid, it is therefore possible in particular to reduce the amount of 3,4'-isomer.

In general, chlorobenzene is used in a stoichiometric amount or in excess, based on the amount of sulfuric acid used.

The amount of catalyst is, as a rule, from 0.01 to 20 mol %, based on 1 mole of sulfuric acid. The reaction takes place particularly advantageously with the use of from 5 to 10 mol % of boric acid of 0.05 to 0.5 mol % of trifluoromethanesulfonic acid, the amounts in each case being based on 1 mole of sulfuric acid.

The reaction products can be isolated in a conventional manner, and the bis-(4-chlorophenyl) sulfone can be purified by a conventional method, for example by selective washing with a solvent, by fractional crystallization or by centrifuging.

The Examples which follow illustrate the process according to the invention.

EXAMPLE 1

In a 5 l reaction kettle made of Hasteloy C 4, 2.03 kg of chlorobenzene and 0.917 kg of 96% strength by weight sulfuric acid were initially taken and were heated to 200° C. under autogenous pressure (4.5 bar). By opening the reducing valve, the chlorobenzene/steam mixture formed was let down, condensation was effected and the chlorobenzene was recycled to the reaction solution By continuously increasing the temperature to 240° C., the pressure was kept at 4.5-5 bar under boiling conditions. After a reaction time of 16 hours, the mixture was cooled to room temperature, the residual chlorobenzene was removed by distillation, the residue was stirred thoroughly in 10 l of water and the remaining solid was filtered off, washed twice with 1 l of water and dried.

Yield: 1.76 kg; 68% (total sulfones)
Isomer content:
4,4': 79%
2,4': 7.5%
3,4': 13.5%

EXAMPLE 2

The procedure was similar to that for Example 1, except that 30 g of boric acid were added and the reaction time was 10 hours.
Yield: 2.17 kg (84%)
Isomer content:
4,4': 84.8%
2,4': 7.8%
3,4': 7.4%

EXAMPLE 3

The procedure was similar to that for Example 1, except that 5 ml of trifluoromethanesulfonic acid were added and the reaction time was 10 hours.
Yield: 1.94 kg (75%)
Isomer content:
4,4': 89.3%
2,4': 5.2%
3,4': 5.5%

We claim:

1. A process for the preparation of bis-(4-chlorophenyl) sulfone by reacting chlorobenzene with sulfuric acid at from 200° to 250° C., wherein a condensing agent selected from the group consisting of boric acid and trifluoromethanesulfonic acid is added.

2. A process as claimed in claim 1, wherein from 5 to 10 mol % of boric acid or from 0.05 to 0.5 mol % of trifluoromethanesulfonic acid is added, the amounts being based in each case on 1 mole of sulfuric acid.

3. A process as claimed in claim 1, wherein the water formed in the reaction is removed from the reaction mixture by azeotropic distillation.

* * * * *